United States Patent
Freitag et al.

(10) Patent No.: US 8,790,819 B1
(45) Date of Patent: Jul. 29, 2014

(54) IMPLANTABLE MEDICAL ASSEMBLY

(75) Inventors: Gary Freitag, East Aurora, NY (US); Dominick Frustaci, Williamsville, NY (US)

(73) Assignee: Greatbatch Ltd., Clarence, NY (US)

( * ) Notice: Subject to any disclaimer, the term of this patent is extended or adjusted under 35 U.S.C. 154(b) by 1683 days.

(21) Appl. No.: 11/869,118

(22) Filed: Oct. 9, 2007

Related U.S. Application Data

(60) Provisional application No. 60/828,397, filed on Oct. 6, 2006.

(51) Int. Cl.
| | | |
|---|---|---|
| *A61N 1/00* | (2006.01) | |
| *A61N 1/32* | (2006.01) | |
| *A61N 1/36* | (2006.01) | |
| *A61N 1/39* | (2006.01) | |
| *A61B 19/00* | (2006.01) | |
| *G09B 23/28* | (2006.01) | |
| *H01M 2/00* | (2006.01) | |
| *H01M 6/00* | (2006.01) | |
| *H01M 10/00* | (2006.01) | |

(52) U.S. Cl.
USPC ........... 429/163; 429/122; 128/897; 434/262; 607/1; 607/2

(58) Field of Classification Search
CPC ........... A61N 1/32; A61N 1/36; A61N 1/362; A61N 1/3605; A61N 1/37205; A61N 1/39; A61B 19/00; G09B 23/28; H01M 2/00; H01M 6/00; H01M 10/00
USPC ........... 128/897; 607/1, 2; 434/262; 429/163, 429/122
See application file for complete search history.

(56) References Cited

U.S. PATENT DOCUMENTS

| | | | | |
|---|---|---|---|---|
| 1,357,126 A | * | 10/1920 | Stretton | 429/164 |
| 3,578,506 A | * | 5/1971 | Chassoux | 429/183 |
| 3,971,673 A | * | 7/1976 | Coueille | 429/171 |
| 3,996,066 A | | 12/1976 | Mead et al. | |
| 4,233,372 A | | 11/1980 | Bro et al. | |
| 4,487,819 A | * | 12/1984 | Koga | 429/82 |
| 4,567,121 A | | 1/1986 | Gilmour | |
| 4,598,466 A | | 7/1986 | Arenas et al. | |
| 5,086,773 A | * | 2/1992 | Ware | 607/2 |

(Continued)

OTHER PUBLICATIONS

Wikipedia (Wikipedia printed Dec. 15, 2011 {http://en.wikipedia.org/wiki/Copper_sulfide}).*

(Continued)

*Primary Examiner* — Patrick Ryan
*Assistant Examiner* — Aaron Greso
(74) *Attorney, Agent, or Firm* — Michael F. Scalise

(57) ABSTRACT

A compact implantable medical assembly is comprised of a medical device connected to an electrochemical cell. The medical device is comprised of a housing enclosing at least one electrical circuit and including an end having a perimeter edge and a contact opening therethrough. The electrochemical cell is comprised of a casing having a sidewall extending to a distal end and a proximal end forming a proximal opening. The proximal casing end is joined to the medical device housing. A glass-to-metal seal supports a terminal pin extending from within the casing through the proximal casing opening and through the contact opening in the end of the housing. The terminal pin is connected to the electrical circuit contained within the housing. That way the cell serves as the power source for the medical device with both the cell and medical device being exposed to body fluid.

19 Claims, 1 Drawing Sheet

(56) References Cited

U.S. PATENT DOCUMENTS

| | | | |
|---|---|---|---|
| 5,139,684 A | | 8/1992 | Kaali et al. |
| 5,188,738 A | | 2/1993 | Kaali et al. |
| 5,306,581 A | | 4/1994 | Taylor et al. |
| 5,545,842 A | * | 8/1996 | Balsells ............... 174/372 |
| 5,643,694 A | | 7/1997 | Heller, Jr. |
| 5,711,988 A | * | 1/1998 | Tsai et al. ............... 427/80 |
| 5,750,286 A | * | 5/1998 | Paulot et al. ............ 429/211 |
| 5,926,362 A | * | 7/1999 | Muffoletto et al. ...... 361/503 |
| 6,010,803 A | | 1/2000 | Heller, Jr. et al. |
| 6,083,710 A | | 7/2000 | Heller et al. |
| 6,121,009 A | | 9/2000 | Heller et al. |
| 6,136,025 A | | 10/2000 | Barbut et al. |
| 6,334,879 B1 | * | 1/2002 | Muffoletto et al. ...... 29/25.03 |
| 6,342,071 B1 | | 1/2002 | Pless |
| 6,569,562 B1 | | 5/2003 | Spillman et al. |
| 6,641,612 B2 | | 11/2003 | Pless |
| 6,670,074 B2 | | 12/2003 | Spillman |
| 6,759,163 B2 | | 7/2004 | Frysz et al. |
| 6,815,286 B2 | * | 11/2004 | Krieger et al. ............ 438/238 |
| 6,984,468 B2 | | 1/2006 | Rubino et al. |
| 7,022,146 B2 | | 4/2006 | Rubino et al. |
| 2001/0049057 A1 | * | 12/2001 | Frustaci et al. ............ 429/176 |
| 2002/0114991 A1 | * | 8/2002 | Hallifax et al. ............ 429/53 |
| 2002/0136943 A1 | | 9/2002 | Warchockl et al. |
| 2004/0023109 A1 | * | 2/2004 | Rusin et al. ............... 429/180 |
| 2004/0059392 A1 | * | 3/2004 | Parramon et al. ......... 607/36 |
| 2005/0255380 A1 | | 11/2005 | Lasater et al. |
| 2007/0117021 A1 | * | 5/2007 | Frustaci et al. ............ 429/238 |
| 2007/0122697 A1 | | 5/2007 | Wutz et al. |
| 2007/0179532 A1 | | 8/2007 | Root et al. |
| 2008/0085451 A1 | * | 4/2008 | Freitag et al. ............. 429/174 |

OTHER PUBLICATIONS

Hawley's Condensed Chemical Dictionary [Hawley's] (14th edition © 2002 Taken as December John Wiley and Sons—Fluid entry; {http://app.knovel.com/web/view/html/show.v/cid:kt0035QQG5/viewerType:html/root_slug:fluid/url_slug:fluid?q=fluid&b-q=fluid&b-subscription=true&b-within-title=true&b-group-by=false&page=1}).*

Real Dictionary (available May 26, 2003 {http://www.realdictionary.com/?q=hermetic}).*

* cited by examiner

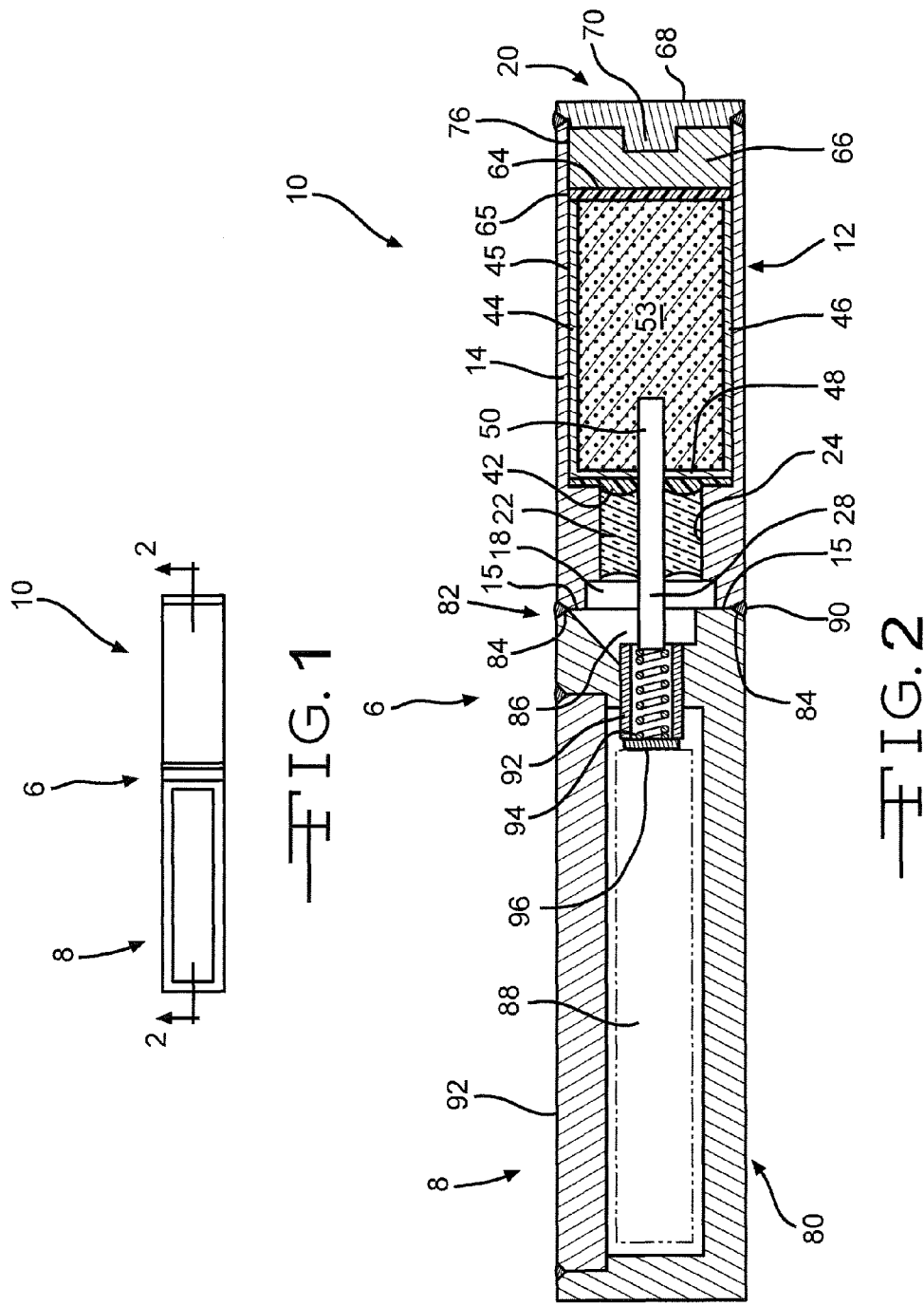

IMPLANTABLE MEDICAL ASSEMBLY

CROSS-REFERENCE TO RELATED PATENT APPLICATION

This application claims priority from U.S. provisional patent application Ser. No. 60/828,397, filed Oct. 6, 2006.

BACKGROUND OF THE INVENTION

1. Field of the Invention

The present invention relates generally to electrochemical cells and implantable medical devices powered by such cells. More particularly, the present invention relates to an electrochemical cell hermetically connected to an implantable or exploratory medical device to form an implantable medical assembly. That way, the cell serves as the power source for the medical device with both the cell and device being exposed to body fluid. The assembly is sufficiently small to be suitable for minimally invasive deployment into a human body, such as for deployment through the vasculature of the body.

2. Description of Related Art

Recent advances in electrochemical cell technology have resulted in cells that have high discharge rate capability and high energy density. These cells are sufficiently compact in size to render them suitable for use in implantable medical devices such as cardiac pacemakers and defibrillators.

U.S. Patent Application Pub. No. 2007/0122697 of Wutz et al., which is assigned to the assignee of the present invention and incorporated herein by reference, describes one such exemplary electrochemical cell comprising a substantially rectangular casing, and a mating terminal connector adapted to be connected to the ferrule and the conductive center pin of the cell. The terminal connector is provided for easily and quickly connecting the cell to a circuit board of the kind found in an implantable medical device, such as a cardiac pacemaker, defibrillator, neurostimulator, or drug pump.

Although the cell of Wutz et al. is suitable for use with many implantable medical devices, continuing medical advances are driving a need for even smaller cells that may be assembled with more compact implantable devices, or with exploratory medical devices that may be deployed into the human vasculature, digestive tract, lungs, or other tissues.

What is needed, therefore, is an electrochemical cell that is further miniaturized and connected to a correspondingly miniaturized medical device to provide an implantable assembly. In such a configuration, the cell of the assembly is external to the medical device, and thus must be exposable to bodily fluids without a detrimental effect to either the cell or the body in which it is deployed.

SUMMARY OF THE INVENTION

The present invention meets the above needs by providing a compact implantable medical assembly comprised of a medical device powered by an electrochemical cell. The medical device is comprised of a housing including an end having a perimeter edge and a contact opening therethrough, and at least one electrical circuit contained within the housing. The electrochemical cell is a casing comprising a sidewall including an end forming a proximal opening in the casing connected to the housing end of the medical device; a glass-to-metal seal disposed in the proximal opening in the casing; a terminal pin extending from within the casing through the glass-to-metal seal and the proximal casing opening and through the contact opening in the housing end, the terminal pin connected to the electrical circuit contained within the device housing; a cathode comprising cathode active material in electrical contact with the terminal pin; an insulator/separator assembly disposed within the casing and enclosing the cathode; an anode comprising anode active material within the casing and prevented from direct physical contact with the cathode by the separator; and an electrolyte activating the anode and the cathode with the cell thereby serving as the power source for the medical device.

In one preferred embodiment, the medical device housing and the cell casing have elongated shapes that are aligned. The end of the cell casing sidewall is preferably contiguous with the perimeter edge of the housing end. The medical device housing is hermetically sealed to the cell casing. This is preferably achieved by connecting and sealing the end of the cell casing sidewall to the perimeter edge of the housing end. This means that both the cell powering the medical device are exposed to body fluid.

In one embodiment, the electrochemical cell is relatively compact in size. The cell is comprised of a casing having a proximal opening, a distal opening, and a sidewall surrounding an enclosed volume. A glass-to-metal seal is disposed in the proximal opening with a terminal pin extending from outside the casing through the glass-to-metal seal and into the enclosed volume of the casing. An insulator is disposed along a first portion of the casing sidewall. A cathode comprising cathode active material is contained within the insulator and in electrical contact with the terminal pin. A separator disc is disposed contiguously with a second portion of the casing sidewall and in contact with an open end of the insulator to thereby envelope the cathode. An anode comprising anode active material is provided in contact with the separator disc and with a third portion of the casing sidewall. An electrolyte is provided within the cell to activate the anode and the cathode, and a lid is sealed to the distal opening of the casing to hermetically enclose the cell contents.

That way, the electrochemical cell connected to the medical device serves as its power source. The medical device may be an implantable device, or an exploratory medical device that may be deployed into the human vasculature, digestive tract, lungs, and other tissues for a shorter time than that of typical implantable devices.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIG. 1 is a side view of an implantable medical assembly comprising a compact electrochemical cell joined to an implantable medical device; and FIG. 2 is a cross-sectional view taken along line 2-2 of FIG. 1.

The present invention will be described in connection with preferred embodiments, however, it should be understood that there is no intent to limit the invention to the embodiments described. On the contrary, the intent is to cover all alternatives, modifications and equivalents as may be included within the scope of the invention as defined by the appended claims.

DETAILED DESCRIPTION OF THE PREFERRED EMBODIMENTS

In describing the present invention, a variety of terms are used. As used herein, the term "implantable" with respect to placement of a device or assembly within a body is meant to include a short-term temporary deployment of the device into the body such as for exploratory purposes, wherein the device or assembly is not necessarily disconnected from a deployment tool; or a longer-term deployment, wherein the device or assembly is released from a surgeon's hand or deployment tool and left in place in the body, with the deployment tool being withdrawn from the body.

The implantable medical assembly of the present invention is comprised of an electrochemical cell that is joined to an implantable medical device. The cell is preferably located outside the casing of the medical device and is, therefore, exposed to bodily fluids when the assembly is implanted in a body. So that no bodily fluids will enter the cell or device, the cell is hermetically sealed to the implantable device. Also, no materials within the cell or the device may leak out into the body.

The cell and the implantable device are preferably both highly miniaturized. Additionally, in one embodiment, the implantable device and the cell are preferably made with an elongate shape and are joined to each other such that the assembly also has an elongate shape. In that manner, the implantable assembly is rendered more suitable for minimally invasive deployment into a human body, such as through the vasculature therein.

Turning now to the drawings, FIGS. 1 and 2 illustrate an exemplary implantable medical assembly of the present invention. The assembly 6 is comprised of an implantable medical device 8 and an electrochemical cell 10. The medical device 8 is comprised of a housing 80 including an end 82 having a perimeter edge 84 and a contact opening 86 therethrough. At least one electrical circuit 88 is contained within the housing 80.

The electrochemical cell 10 of the assembly 6 is comprised of a casing 12 comprising a side wall 14 including an end 15 forming a proximal opening 18 in the casing 12. A glass-to-metal seal 22 is disposed adjacent to the proximal opening 18 and within the casing 12. A terminal pin 28 extends from within the casing 12 through the glass-to-metal seal 22 and proximal opening 18 of the casing 12. A cathode comprising cathode active material 53 is disposed within the casing and is in electrical contact with the terminal pin 28. An insulator 44 and a separator disc 64 seated on the open end of the insulator are also disposed within the casing 12 and enclose the cathode, thereby physically segregating it from the anode. The anode comprises anode active material 66. An electrolyte (not shown) is provided to activate the anode and the cathode.

To provide the medical assembly 6, the implantable medical device 8 is connected to the electrochemical cell 10.

When device 8 is connected with cell 10, the terminal pin 28 extends through the contact opening 86 in the end 82 of the housing 80 and is connected to the electrical circuit 88 contained within the housing 80. The electrical connection of terminal pin 28 to circuit 88 may include a conductive spring 92 contained within a housing tube 94, and a contact plate 96.

In a preferred embodiment, end 15 of cell 10 is connected to end 82 of medical device 8 by welding. Weld 90 is formed around the entire perimeter of the abutted ends 15 and 82, and thus provides a hermetic seal of the device housing 80 to the cell casing 12. The shapes of the cell end 15 and the device end 82 are preferably matched to each other. That makes it is easier to form the weld 90 between them. Additionally, matching the respective ends provides a smooth transition between the cell 10 and the device 8, thereby providing a streamlined and more "user friendly" shape for the purpose of deployment of the assembly into a body.

In one preferred embodiment shown in FIG. 2, the medical device housing 80 and the cell casing 12 have elongated shapes aligned with each other. This feature further provides the above streamlined shape that is advantageous for deployment into a body, such as into the vasculature. The end 15 of the cell casing sidewall 14 is contiguous with the perimeter edge 84 of the end 82 of the device housing 80. The device housing 80 can then be easily sealed to the cell casing 12 by weld 90.

The medical device housing 80 and the cell casing 12 may be provided in various shapes including cylindrical, rectangular, and prismatic. The housing 80 and casing 12 may be made from a variety of metals, including titanium, stainless steel, or various alloys such as Ti—Al—V, Ti—Al—Nb, Ti-13NB-13Zr, or Ti—Mo—Zr—Fe.

The present invention is adaptable to a variety of medical devices including cardiac pacemakers, defibrillators, neurostimulators, drug delivery devices, implantable sensors of a wide variety of physiological parameters including blood gases, pressure, received radiation, and the like. Referring again to FIG. 2, the medical device may further include an active surface 92. The active surface 92 may receive or transmit mechanical, thermal, electrical, and/or light energy for the purposes of sensing conditions, or affecting conditions within the body (not shown) in which the medical assembly 6 is deployed.

In one embodiment, the electrochemical cell 10 is as disclosed in U.S. patent application Ser. No. 11/868,593 filed Oct. 8, 2007, which is assigned to the assignee of the present invention and incorporated herein by reference. In such an embodiment, cell 10 includes a casing 12 comprised of a sidewall 14 surrounding an enclosed volume 16. The casing 12 has a proximal opening 18 and a distal opening 20 at the respective ends of the sidewall 14. A glass-to-metal seal 22 is disposed in the proximal opening 18 and within the enclosed casing volume. A terminal pin 28 extends from outside the casing 12 through the proximal opening 18 and into the enclosed casing volume. The terminal pin 28 forms an annular space with a narrowed region 24 of the casing sidewall 14. A glass-to-metal seal 22 is formed within this annulus and provides a hermetic seal between the terminal pin 28 and the casing 12.

An insulator 44 is disposed along a first portion 45 of the casing sidewall. The insulator 44 can be of any of the hereinafter discussed materials that are suitable for the separator, although it is preferably of polyethylenetetrafluoroethylene (ETFE). A separator is of a material that permits ionic flow there through while maintaining physical separation between the opposite polarity active materials. Likewise, the insulator must maintain physical segregation between the anode and the cathode, but it does not need to permit ionic flow because the casing sidewall is directly opposite the cathode active material contained inside it, as will be discussed presently.

The insulator 44 is preferably formed as a bag having a sidewall 46 and a bottom 48, through which the proximal end 50 of the terminal pin 28 protrudes. Alternatively, insulator 44 can be formed as a sleeve, with its inner edge seated into an elastomeric material 42. Use of the elastomeric material 42 is preferred because it fills any small void formed between the terminal pin and the casing at the inner surface 52 of the GTMS 22. The elastomeric material also seals any gap that is present between the terminal pin and the insulator 44, thereby allowing for greater positional and size variability of the through hole in the bag bottom 48, if such is provided. In that manner, loose particles of cathode active material 53 are prevented from bypassing the insulator and making contact with the casing. The elastomeric material 42 is preferably a polysiloxane that cures to a solid at room temperature.

A cathode comprising the cathode active material 53, such as silver vanadium oxide in a powdered form, is contained within the insulator 44 and is in electrical contact with the terminal pin 28. Other cathode active materials that are useful with the present invention include copper silver vanadium oxide (CSVO), $V_2O_5$, $MnO_2$, $LiCoO_2$, $LiNiO_2$, $LiMn_2O_4$, $TiS_2$, $Cu_2S$, FeS, $FeS_2$, copper oxide, copper vanadium oxide, $Ag_2O$, $Ag_2O_2$, $CuF_2$, $Ag_2CrO_4$, $MnO_2$, and mixtures thereof. In any event, the cathode active material is typically formed into a mixture of about 1% to 5% of a conductive diluent and about 1% to 5% of a binder material, by weight, prior to being used in the cell. Suitable conductive diluents include acetylene black, carbon black and/or graphite. Metals such as nickel, aluminum, titanium and stainless steel in powder form are also useful as conductive diluents.

A suitable binder material is preferably a thermoplastic polymeric material. The term thermoplastic polymeric material is used in its broad sense and any polymeric material which is inert in the cell and which passes through a thermoplastic state, whether or not it finally sets or cures, is included within the term "thermoplastic polymer". Representative binder materials include polyethylene, polypropylene, polyimide, and fluoropolymers such as fluorinated ethylene, fluorinated propylene, polyvinylidene fluoride (PVDF), and polytetrafluoroethylene (PTFE). Natural rubbers are also useful as the binder material with the present invention.

A separator disc 64 is disposed contiguously with a second portion 65 of the casing sidewall 14 and in contact with the cathode at the open end of the insulator 44. The separator disc 64 is of electrically insulative material that is chemically unreactive with the anode and cathode active materials and both chemically unreactive with and insoluble in the electrolyte that is subsequently added to the cell. In addition, the separator material has a degree of porosity sufficient to allow flow there through of the electrolyte during the electrochemical reaction of the cell. Illustrative separator materials include fabrics woven from fluoropolymeric fibers including polyvinylidine fluoride, polyethylenetetra-fluoroethylene, and polyethylenechlorotrifluoroethylene used either alone or laminated with a fluoropolymeric microporous film, non-woven glass, polypropylene, polyethylene, glass fiber materials, ceramics, polytetrafluoroethylene membrane commercially available under the designation ZITEX (Chemplast Inc.), polypropylene membrane commercially available under the designation CELGARD (Celanese Plastic Company, Inc.), a membrane commercially available under the designation DEXIGLAS (C. H. Dexter, Div., Dexter Corp.), and a membrane commercially available under the designation TONEN®.

An anode comprising anode active material 66, preferably lithium, is provided in contact with the separator disc 64 and with a third portion 76 of the casing sidewall 14.

An electrolyte (not shown) is provided within the cell to activate the anode and the cathode, and a lid 68 is sealed to the distal casing opening 20 to hermetically enclose the contents of the cell 10. A suitable electrolyte has an inorganic, ionically conductive salt dissolved in a nonaqueous solvent, and more preferably, the electrolyte includes an ionizable lithium salt dissolved in a mixture of aprotic organic solvents comprising a low viscosity solvent and a high permittivity solvent. The inorganic, ionically conductive salt serves as the vehicle for migration of the anode ions to intercalate or react with the cathode active materials. Known lithium salts that are useful as a vehicle for transport of alkali metal ions from the anode to the cathode include $LiPF_6$, $LiBF_4$, $LiAsF_6$, $LiSbF_6$, $LiClO_4$, $LiO2$, $LiAlCl_4$, $LiGaCl_4$, $LiC(SO_2CF_3)_3$, $LiN(SO_2CF_3)_2$, LiSCN, $LiO_3SCF_3$, $LiC_6FSO_3$, $LiO_2CCF_3$, $LiSO_6F$, $LiB(C_6H_5)_4$, $LiCF_3SO_3$, and mixtures thereof.

Suitable low viscosity solvents invention include esters, linear and cyclic ethers and dialkyl carbonates such as tetrahydrofuran (THF), methyl acetate (MA), diglyme, triglyme, tetraglyme, dimethyl carbonate (DMC), 1,2-dimethoxyethane (DME), 1,2-diethoxyethane (DEE), 1-ethoxy,2-methoxyethane (EME), ethyl methyl carbonate, methyl propyl carbonate, ethyl propyl carbonate, diethyl carbonate, dipropyl carbonate, and mixtures thereof, and suitable high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methyl-pyrrolidinone (NMP), and mixtures thereof. The preferred electrolyte for a lithium anode is 0.8M to 1.5M $LiAsF_6$ or $LiPF_6$ dissolved in a 50:50 mixture, by volume, of propylene carbonate as the preferred high permittivity solvent and 1,2-dimethoxyethane as the preferred low viscosity solvent.

The lid 68 of the cell may include a protrusion 70 that is in interfering contact with the anode. The protrusion 70 may extend substantially from the base of the lid 68 and be embedded in the anode active material 66. The lid 68 may also apply a compressive force against the anode, the separator disc and the cathode.

It is, therefore, apparent that there has been provided, in accordance with the present invention, an implantable medical assembly comprising a compact electrochemical cell joined to an implantable medical device. In that manner, the cell serves as the power source for the implantable device without being contained or housed inside the medical device, which is typically how an implantable medical device is built. Instead, the cell and medical device are joined or connected end-to-end with each being exposed to body fluid. That means that the connection between the cell and medical device must be hermetic.

While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. An implantable medical assembly,
which comprises:
a) a medical device comprising:
   i) an electrically conductive device housing comprising a device housing end surrounding a device contact opening, and
   ii) at least one electrical circuit contained within and electrically connected to the device housing; and
b) an electrochemical cell comprising:
   i) an electrically conductive cell casing comprising a casing sidewall extending from a distal casing opening to a proximal casing opening;
   ii) an electrically non-conductive insulator disposed along a first interior portion of the casing sidewall adjacent to the proximal casing opening;
   iii) a cathode active material contained within the insulator;
   iv) a separator disc comprising a polymeric material that permits ionic flow between opposed first and second major disc faces spaced apart from each other by a disc thickness providing a disc edge that is contiguous with a second interior portion of the casing sidewall, wherein the first major disc face is in contact with the cathode active material contained within the insulator;

v) an anode active material in direct contact with the second major disc face and with a third interior portion of the casing sidewall adjacent to the distal casing opening so that the cell casing serves as an anode terminal, wherein the first and second major disc faces are continuous surfaces that prevent the anode active material from physical contact with the cathode active material;

vi) a lid sealed to the distal casing opening;

vii) a glass-to-metal seal hermetically sealed to the proximal casing opening, wherein the glass-to-metal seal comprises a terminal pin extending through a sealing glass in the proximal casing opening and through the device contact opening in the device housing end, the terminal pin having a proximal pin portion within the cell casing in contact with the cathode active material to thereby serve as a cathode terminal and a distal pin portion as a positive contact electrically connected to the at least one electrical circuit contained within the device housing; and viii) an electrolyte activating the anode active material and the cathode active material, c) wherein the electrically conductive cell casing at the proximal casing opening is directly electrically connected to the device housing at the device contact opening so that there is electrical continuity from the cell casing as the anode terminal to the device housing as a negative electrical contact connected to the at least one electrical circuit and then the terminal pin as the positive electrical contact and the cathode terminal to thereby power the at least one electrical circuit in the device housing.

2. The implantable medical assembly of claim 1 wherein the casing sidewall is comprised of a narrowed region contiguous with the glass-to-metal seal.

3. The implantable medical assembly of claim 1 further comprising an elastomeric material that joins the separator to the glass-to-metal seal.

4. The implantable medical assembly of claim 3 wherein the separator is formed as a bag having a sidewall and a bottom, and wherein the bottom is joined to the glass-to-metal seal by the elastomeric material.

5. The implantable medical assembly of claim 1 wherein the separator includes an outer separator edge and the separator disc is in contact with the outer separator edge.

6. The implantable medical assembly of claim 1 wherein the lid comprises a protrusion in interference contact with the anode active material.

7. The implantable medical assembly of claim 6 wherein the protrusion is embedded in the anode active material.

8. The implantable medical assembly of claim 1 wherein the lid applies a compressive force to the anode active material, the separator disc, and the cathode active material.

9. The implantable medical assembly of claim 1 further comprising a flange at the proximal opening of the casing, the flange contacted to the device housing end.

10. The implantable medical assembly of claim 1 wherein the cathode active material is of a powder form pressed into the insulator.

11. The implantable medical assembly of claim 1 wherein of the cell casing is of an electrically conductive material selected from the group consisting of titanium, stainless steel, Ti—Al—V, Ti—Al—Nb, Ti-13NB-13Zr, and Ti—Mo—Zr—Fe.

12. An implantable medical assembly, which comprises:

a) a medical device comprising:
  i) an electrically conductive device housing comprising a device housing end surrounding a device contact opening, and
  ii) at least one electrical circuit contained within and electrically connected to the device housing; and b) an electrochemical cell comprising:
  i) an electrically conductive cell casing comprising a casing sidewall extending from a distal casing opening to a proximal casing opening;
  ii) an electrically non-conductive insulator disposed along a first interior portion of the casing sidewall adjacent to the proximal casing opening;
  iii) a first electrode active material contained within the insulator;
  iv) a separator disc comprising a polymeric material that permits ionic flow between opposed first and second major disc faces spaced apart from each other by a disc thickness providing a disc edge that is contiguous with a second interior portion of the casing sidewall, wherein the first major disc face is in contact with the first electrode active material contained within the insulator;
  v) a second, counter electrode active material in direct contact with the second major disc face and with a third interior portion of the casing sidewall adjacent to the distal casing opening so that the casing serves as a second electrode terminal, wherein the first and second major disc faces are continuous surfaces that prevent the first electrode active material from physical contact with the second electrode active material;
  vi) a lid sealed to the distal casing opening;
  vii) a glass-to-metal seal hermetically sealed to the proximal casing opening, wherein the glass-to-metal seal comprises a terminal pin extending through a sealing glass in the proximal casing opening and through the device contact opening in the device housing end, the terminal pin having a proximal pin portion within the cell casing in contact with the first electrode active material to thereby serve as a first electrode terminal and a distal pin portion as a first electrical contact electrically connected to the at least one electrical circuit contained within the device housing; and
  viii) an electrolyte activating the first and second electrode active materials, c) wherein the electrically conductive cell casing at the proximal casing opening is directly electrically connected to the device housing at the device contact opening so that there is electrical continuity from the cell casing as the second electrode terminal to the device housing as a second electrical contact connected to the at least one electrical circuit and then the terminal pin as the first electrical contact and the first electrode terminal to thereby power the at least one electrical circuit in the device housing.

13. An implantable medical assembly, which comprises:

a) a medical device comprising:
  i) an electrically conductive device housing comprising a device housing end surrounding a device contact opening, and ii) at least one electrical circuit contained within and electrically connected to the device housing; and
b) an electrochemical cell comprising:
i) an electrically conductive cell casing comprising a casing sidewall extending from a distal casing opening to a proximal casing opening;
ii) an electrically non-conductive insulator disposed along a first interior portion of the casing sidewall adjacent to the proximal casing opening;
iii) a first electrode active material contained within the insulator;
iv) a separator disc comprising a polymeric material that permits ionic flow between opposed first and second major disc faces spaced apart from each other by a disc thickness providing a disc edge that is contiguous with a second interior portion of the casing sidewall, wherein the first major disc face is in contact with the first electrode active material contained within the insulator;
v) a second, counter electrode active material in direct contact with the second major disc face and with a third interior portion of the casing sidewall adjacent to the distal casing opening so that the casing serves as a second electrode terminal, wherein the first and second major disc faces are continuous surfaces that prevent the first electrode active material from physical contact with the second electrode active material;
vi) a lid sealed to the distal casing opening;
vii) a glass-to-metal seal hermetically sealed to the proximal casing opening, wherein the glass-to-metal seal comprises a terminal pin extending through a sealing glass in the proximal casing opening and through the device contact opening in the device housing end, and wherein the terminal pin extends along a pin axis from a proximal pin portion within the cell casing in contact with the first electrode active material to a distal pin portion in the device housing;
viii) an electrolyte activating the first and second electrode active materials; and
c) a spring contact having a spring length extending along a spring axis aligned with the pin axis, wherein the spring biases between a proximal spring end in electrical contact with the distal pin portion and a distal spring end as a first electrical contact with the at least one electrical circuit within the device housing,
d) wherein the electrically conductive cell casing at the proximal casing opening is directly electrically connected to the device housing at the device contact opening so that there is electrical continuity from the cell casing as the second electrode terminal to the device housing as a second electrical contact connected to the at least one electrical circuit and then the terminal pin and spring as the first electrical contact and the first electrode terminal to thereby power the at least one electrical circuit in the device housing.

14. The implantable medical assembly of claim 1 wherein the anode active material is lithium.

15. The implantable medical assembly of claim 1 wherein the cathode active material is selected from the group consisting of silver vanadium oxide, copper silver vanadium oxide (CSVO), $V_2O_5$, $MnO_2$, $LiCoO_2$, $LiNiO_2$, $LiMn_2O_4$, $TiS_2$, $Cu_2S$, $FeS$, $FeS_2$, copper oxide, copper vanadium oxide, $Ag_2O$, $Ag_2O_2$, $CuF_2$, $Ag_2CrO_4$, $MnO_2$, and mixtures thereof.

16. The implantable medical assembly of claim 1 wherein the cathode active material is mixed with about 1% to 5% of a conductive diluent and about 1% to 5% of a binder material, by weight, prior to being used in the cell.

17. The implantable medical assembly of claim 16 wherein the conductive diluent is selected from the group consisting of acetylene black, carbon black, graphite, powdered aluminum, powdered titanium, and powdered stainless steel.

18. The implantable medical assembly of claim 13 wherein the spring is a coil spring.

19. The implantable medical assembly of claim 13 wherein the lid comprises a protrusion in interference contact with the second electrode active material.

\* \* \* \* \*

UNITED STATES PATENT AND TRADEMARK OFFICE
CERTIFICATE OF CORRECTION

| | | |
|---|---|---|
| PATENT NO. | : 8,790,819 B1 | Page 1 of 1 |
| APPLICATION NO. | : 11/869118 | |
| DATED | : July 29, 2014 | |
| INVENTOR(S) | : Gary Freitag and Dominick Frustaci | |

It is certified that error appears in the above-identified patent and that said Letters Patent is hereby corrected as shown below:

In the claims

Column 7, line 67 after the word "wherein" delete the word "of"

Signed and Sealed this
Sixteenth Day of February, 2016

Michelle K. Lee
*Director of the United States Patent and Trademark Office*